United States Patent
Sun et al.

(10) Patent No.: US 11,478,198 B2
(45) Date of Patent: Oct. 25, 2022

(54) PHYSIOLOGICAL PARAMETER SIGNAL FUSION PROCESSING METHOD, APPARATUS, AND SYSTEM

(71) Applicant: Shenzhen Mindray Bio-Medical Electronics Co., Ltd., Shenzhen (CN)

(72) Inventors: Zehui Sun, Shenzhen (CN); Bailei Sun, Shenzhen (CN); Chaocheng Xie, Shenzhen (CN); Jianwei Su, Shenzhen (CN); Sanchao Liu, Shenzhen (CN); Wenyu Ye, Shenzhen (CN); Lihan Liu, Shenzhen (CN); Ming Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1012 days.

(21) Appl. No.: 15/998,515

(22) Filed: Aug. 16, 2018

(65) Prior Publication Data
US 2019/0000397 A1    Jan. 3, 2019

Related U.S. Application Data

(63) Continuation of application No. PCT/CN2016/074031, filed on Feb. 18, 2016.

(51) Int. Cl.
*G01N 33/50* (2006.01)
*A61B 5/00* (2006.01)
(Continued)

(52) U.S. Cl.
CPC ........ *A61B 5/7225* (2013.01); *A61B 5/02055* (2013.01); *A61B 5/7282* (2013.01);
(Continued)

(58) Field of Classification Search
CPC ............ A61B 5/02055; A61B 5/14542; A61B 5/7225; A61B 5/7282; A61B 5/743; G16H 40/20; G16H 40/63; G16H 50/20
(Continued)

(56) References Cited

U.S. PATENT DOCUMENTS 5,626,140 A * 5/1997 Feldman .............. G06K 9/6293
    600/483
2005/0273940 A1* 12/2005 Petrosenko ........ A61G 7/05769
    5/722
(Continued)

FOREIGN PATENT DOCUMENTS

CN    2785540 Y    6/2006
CN    101272734 A    9/2008
(Continued)

*Primary Examiner* — Naomi J Small
(74) *Attorney, Agent, or Firm* — Kory D. Christensen

(57) ABSTRACT

Disclosed are methods, apparatuses, and systems for performing physiological parameter signal fusion. By respectively analyzing a plurality of input physiological parameter signals, and obtaining a feature of each physiological parameter signal; according to the feature of each physiological parameter signal, obtaining and outputting a fusion state of the plurality of the physiological parameter signals; if the fusion state is a fusion of the at least two physiological parameter signals with the first physiological parameter signal is dominant, highlighting the first physiological parameter signal; and if the fusion state is a fusion of the at least two physiological parameter signals with the second physiological parameter signal is dominant, highlighting the second physiological parameter signal.

11 Claims, 10 Drawing Sheets

(51) Int. Cl.
*G16H 40/20* (2018.01)
*G16H 40/63* (2018.01)
*G16H 50/20* (2018.01)
*A61B 5/0205* (2006.01)
*A61B 5/145* (2006.01)

(52) U.S. Cl.
CPC .......... *A61B 5/743* (2013.01); *G16H 40/20* (2018.01); *G16H 40/63* (2018.01); *G16H 50/20* (2018.01); *A61B 5/14542* (2013.01)

(58) Field of Classification Search
USPC .......................................................... 702/19
See application file for complete search history.

(56) References Cited

U.S. PATENT DOCUMENTS

| | | | | |
|---|---|---|---|---|
| 2006/0195159 | A1* | 8/2006 | Bradley | A61N 1/36185 607/48 |
| 2008/0108884 | A1* | 5/2008 | Kiani | A61B 5/6887 600/301 |
| 2009/0285788 | A1* | 11/2009 | Wilson | C12N 15/1086 506/10 |
| 2013/0002264 | A1* | 1/2013 | Garber | A61B 5/08 324/600 |
| 2014/0275832 | A1* | 9/2014 | Muehlsteff | A61B 5/6889 600/301 |
| 2015/0173670 | A1* | 6/2015 | Simon | A61B 5/746 702/150 |
| 2015/0372433 | A1* | 12/2015 | Lisogurski | A61B 5/14552 439/224 |
| 2016/0001088 | A1* | 1/2016 | Averina | A61N 1/36535 607/18 |
| 2016/0192887 | A1 | 7/2016 | Sun et al. | |

FOREIGN PATENT DOCUMENTS

| | | |
|---|---|---|
| CN | 103052956 A | 4/2013 |
| CN | 103181752 A | 7/2013 |
| CN | 104887198 A | 9/2015 |
| WO | WO2015/022604 A2 | 2/2015 |
| WO | WO2015035764 A1 | 3/2015 |
| WO | WO2017/139946 A1 | 8/2017 |

* cited by examiner

| State | Scheme 1 | Scheme 2 | Scheme 3 | Scheme 4 |
|---|---|---|---|---|
| Being homologous but not fused | E[R][ ][ ]<br>s[ ][ ][G] | E[R][ ][ ]<br>s[ ][ ][G] | E[R][ ][ ]<br>s[ ][ ][G] | E[R][ ][ ]<br>s[ ][ ][G] |
| Being homologous, and signal E being fused by signal S | E[R][ ][ ]<br>(s[ ][ ][G]) | E[R][ ][ ]<br>(s[ ][ ][G]) | E[R][ ][ ]<br>(s[ ][ ][G]) | E[R][ ][ ]<br>(s[ ][ ][G]) |
| Being homologous, and signal S being fused by signal E | (E[ ][ ][G])<br>s[R][ ][ ] | (E[ ][ ][G])<br>s[R][ ][ ] | (E[ ][ ][G])<br>s[R][ ][ ] | (E[ ][ ][G])<br>s[R][ ][ ] |
| Being non-homologous/ single parameter | E[R][ ][ ]<br>s[ ][ ][G] | E[R][ ][ ]<br>———<br>s[ ][ ][G] | (E[R][ ][ ]<br>s[ ][ ][G]) | Hiding |

FIG. 13

| State | Scheme 1 | Scheme 2 | Scheme 3 |
|---|---|---|---|
| Being homologous but not fused | E[R][ ][ ]<br>s[ ][ ][G] | E[R][ ][ ]<br>s[ ][ ][G] | E[R][ ][ ]<br>s[ ][ ][G] |
| Being homologous, and signal E being fused by signal S | (E[R][ ][ ]<br>s[ ][ ][G]) | (E[R][ ][ ]<br>s[ ][ ][G]) | (E[R][ ][ ]<br>s[ ][ ][G]) |
| Being homologous, and signal S being fused by signal E | (E[ ][ ][G]<br>s[R][ ][ ]) | (E[ ][ ][G]<br>s[R][ ][ ]) | (E[ ][ ][G]<br>s[R][ ][ ]) |
| Being non-homologous/ single parameter | E[R][ ][ ]<br>s[ ][ ][G] | E[R][ ][ ]<br>———<br>s[ ][ ][G] | Hiding |

FIG. 14

PHYSIOLOGICAL PARAMETER SIGNAL FUSION PROCESSING METHOD, APPARATUS, AND SYSTEM

CROSS-REFERENCE TO RELATED APPLICATIONS

This application is a continuation of PCT App. No. PCT/CN2016/074031, filed Feb. 18, 2018, for PHYSIOLOGICAL PARAMETER SIGNAL FUSION PROCESSING METHOD, APPARATUS, AND SYSTEM, which is incorporated herein by reference.

TECHNICAL FIELD

The present disclosure relates to medical instruments and, in particular, to a physiological parameter signal fusion processing method, apparatus and system.

BACKGROUND

Patient monitors are typically usually used to monitor various physiological parameters, including electrocardiogram, blood oxygen, blood pressure, and body temperature. However, current multi-parameter monitors still independently measure and analyze various parameters, and are susceptible to interference (such as electromagnetic noise) in a monitoring environment, poor contact with probes, patient motion during the measurement of a single parameter, all of which may cause incorrect results and false alarms. Frequent occurrences of certain false alarms lead to alarm fatigue of medical personnel, and thus affect the timely determination by medical personnel of the patient's condition, thereby delaying diagnosis and treatment. In addition, there is a lack of an effective mechanism for analyzing and processing of relationships among various parameters. The parameters are now independent and decentralized and even trigger conflicting alarms, such that medical personnel are distracted, confused about monitoring results, distrust monitoring devices, and not sensitive to dangerous patient states, thereby increasing the potential clinical risk for the patient. There is a lack of a simple and intuitive method for expressing the results of comprehensive analysis of the parameters, affecting the rapid and reliable determination of the patient's condition by medical personnel.

SUMMARY

The present disclosure provides a physiological parameter signal fusion processing method, apparatus and system that provides a joint determination mechanism among various physiological parameters, reducing the false alarms caused by an interfered with single parameter measurement, and help doctors to easily and rapidly determine changes in key physiological information about a patient.

In a first aspect, a physiological parameter signal fusion processing method includes: respectively analyzing at least two input physiological parameter signals, so as to obtain a feature of each of the physiological parameter signals; obtaining a fusion state of the at least two physiological parameter signals according to the features of the at least two physiological parameter signals, with the fusion state including a fusion of the at least two physiological parameter signals with a first physiological parameter signal is dominant, and a fusion of the at least two physiological parameter signals with a second physiological parameter signal is dominant; and outputting the fusion state of the at least two physiological parameter signals. If the fusion state is the fusion of the at least two physiological parameter signals with the first physiological parameter signal is dominant, the output may include highlighting the first physiological parameter signal, and if the fusion state is the fusion of the at least two physiological parameter signals with the second physiological parameter signal is dominant, the output may include highlighting the second physiological parameter signal.

In combination with the first aspect, in a first embodiment, the outputting of the fusion state of the at least two physiological parameter signals includes highlighting, by means of a color, a graphic and/or a set identifier, the physiological parameter signal which is dominant.

In combination with the first aspect, in a second embodiment, the method further includes: calculating a signal quality index for each of the physiological parameter signals according to the feature of each of the physiological parameter signals; the obtaining of a fusion state of the at least two physiological parameter signals according to the features of the at least two physiological parameter signals includes: comparing the signal quality index for each of the physiological parameter signals, so as to obtain the fusion state of the at least two physiological parameter signals; and the outputting of the fusion state of the at least two physiological parameter signals includes highlighting the signal quality index for the physiological parameter signal which is dominant.

In combination with the second embodiment of the first aspect, in a third embodiment, the signal quality index is represented by a background color set on a signal square lattice graph, a traffic signal graph or a physiological parameter signal waveform graph.

In combination with the first aspect or the first embodiment of the first aspect or the second embodiment of the first aspect or the third embodiment of the first aspect, in a fourth embodiment, the method further includes performing a homology determination on the at least two physiological parameter signals according to the features of the at least two physiological parameter signals, so as to obtain a homology determination result for the at least two physiological parameter signals, with the homology determination result including being homologous and non-homologous.

In combination with the fourth embodiment of the first aspect, in a fifth embodiment, the method further includes: if the homology determination result indicates being homologous, outputting the fusion state and the homology determination result; and the method further includes: if the homology determination result indicates being non-homologous, identifying the at least two physiological parameter signals as being non-homologous.

In combination with the first aspect, in a sixth embodiment of the first aspect, the method further includes: calculating a parameter for each of the physiological parameter signals according to the feature of each of the physiological parameter signals; and correcting the parameter for each of the physiological parameter signals according to the fusion state of the at least two physiological parameter signals, so as to obtain a merging parameter for each of the physiological parameter signals.

In a second aspect, a physiological parameter signal fusion processing apparatus or system is provided, the physiological parameter signal fusion processing apparatus or system having the functions of implementing the behaviors of the physiological parameter signal fusion processing apparatus or system in the method above. The functions may be implemented by hardware, and may also be implanted by hardware executing corresponding software stored in a non-transitory computer-readable medium. The hardware or software includes one or more units corresponding to the functions above.

In one embodiment, a physiological parameter signal fusion processing apparatus includes: an analyzer for respectively analyzing at least two input physiological parameter signals, so as to obtain a feature of each of the physiological parameter signals; a fusion unit for obtaining a fusion state of the at least two physiological parameter signals according to the features of the at least two physiological parameter signals, with the fusion state including a fusion of the at least two physiological parameter signals with a first physiological parameter signal is dominant, and a fusion of the at least two physiological parameter signals with a second physiological parameter signal is dominant; and an output unit for outputting the fusion state of the at least two physiological parameter signals, the outputting including: if the fusion state is the fusion of the at least two physiological parameter signals with the first physiological parameter signal is dominant, highlighting the first physiological parameter signal, and if the fusion state is the fusion of the at least two physiological parameter signals with the second physiological parameter signal is dominant, highlighting the second physiological parameter signal.

In another embodiment, a physiological parameter signal fusion processing system includes: an input apparatus, an output apparatus and a processor, wherein the input apparatus is used for inputting at least two physiological parameter signals; the processor is used for respectively analyzing at least two input physiological parameter signals, so as to obtain a feature of each of the physiological parameter signals, and obtaining a fusion state of the at least two physiological parameter signals according to the features of the at least two physiological parameter signals, with the fusion state including a fusion of the at least two physiological parameter signals with a first physiological parameter signal is dominant, and a fusion of the at least two physiological parameter signals with a second physiological parameter signal is dominant; and outputting the fusion state of the at least two physiological parameter signals, the outputting including: if the fusion state is the fusion of the at least two physiological parameter signals with the first physiological parameter signal is dominant, highlighting the first physiological parameter signal, and if the fusion state is the fusion of the at least two physiological parameter signals with the second physiological parameter signal is dominant, highlighting the second physiological parameter signal.

The implementation of the physiological parameter signal fusion processing method, apparatus, and system provided in the embodiments of the present disclosure has the following beneficial effects. By respectively analyzing a plurality of input physiological parameter signals to obtain a feature of each of the physiological parameter signals, obtaining and outputting a fusion state of the plurality of physiological parameter signals according to the feature of each of the physiological parameter signals, highlighting, if the fusion state is a fusion of the at least two physiological parameter signals with a first physiological parameter signal is dominant, the first physiological parameter signal, and highlighting, if the fusion state is a fusion of the at least two physiological parameter signals with a second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by an interfered with single parameter measurement. This results in more reliable information and helps doctors to easily and rapidly determine the change in key physiological information about a patient.

BRIEF DESCRIPTION OF THE DRAWINGS

FIG. 12 is a schematic diagram of another exemplary signal quality index;

FIG. 13 is a schematic diagram of yet another exemplary state synthesis result;

FIG. 14 is a schematic diagram of yet another exemplary state synthesis result;

DETAILED DESCRIPTION

The technical solutions of the embodiments of the present application will be described below in conjunction with the drawings of the embodiments of the present disclosure. The embodiments described are merely some embodiments of the present disclosure and are not all the possible embodiments. Based on the embodiments given in the present disclosure, all other embodiments that would be obtained by those of ordinary skill in the art without expending inventive effort shall all fall within the scope of protection of the present disclosure.

At present, there is no monitoring device to display a multi-parameter fusion state on an interface to present a fusion process. The embodiments of the present disclosure provide a physiological parameter signal fusion processing method, apparatus, and system. By means of respectively analyzing a plurality of input physiological parameter signals to obtain a feature of each of the physiological parameter signals, obtaining and outputting a fusion state of the plurality of physiological parameter signals according to the feature of each of the physiological parameter signals, highlighting, if the fusion state is a fusion of the at least two physiological parameter signals with a first physiological parameter signal is dominant, the first physiological parameter signal, and highlighting, if the fusion state is a fusion of the at least two physiological parameter signals with a second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient.

Figure 1:
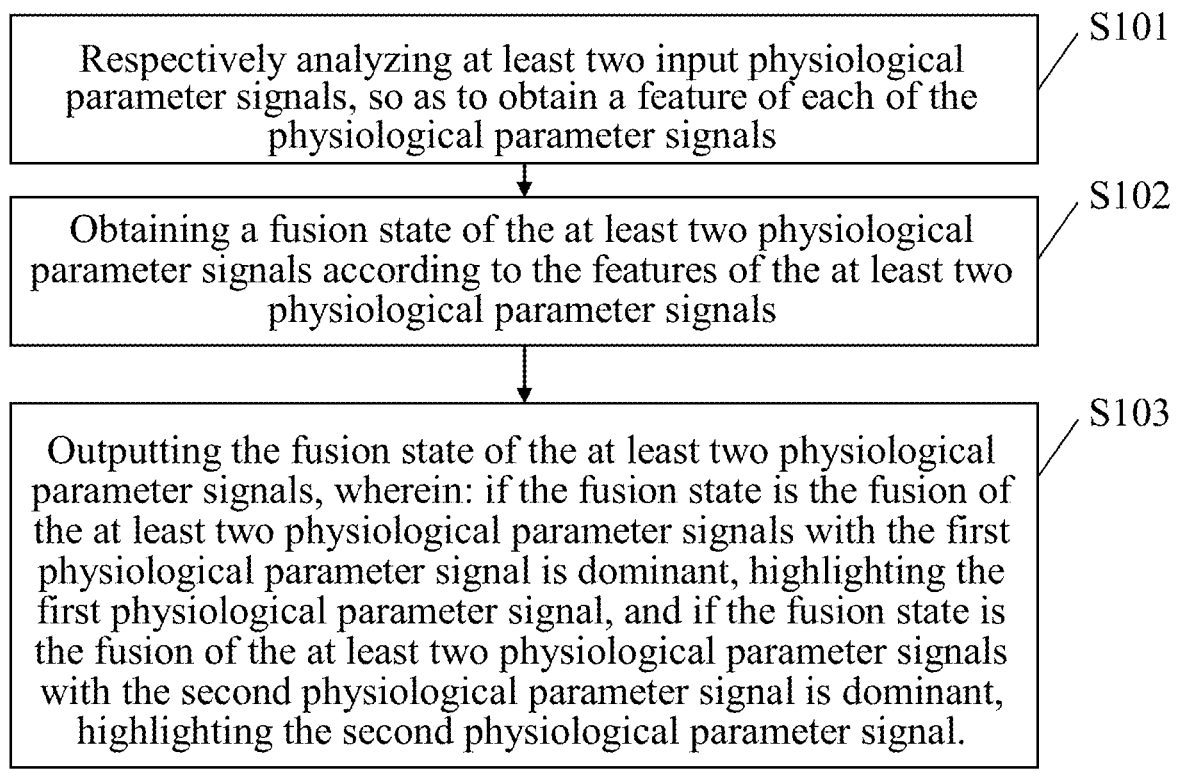
FIG. 1 is a schematic flow diagram of a physiological parameter signal fusion processing method.

FIG. 1 is a schematic flow diagram of a physiological parameter signal fusion processing method provided in the embodiments of the present disclosure. The method includes the steps of:

Step S101, respectively analyzing at least two input physiological parameter signals, so as to obtain a feature of each of the physiological parameter signals.

The physiological parameter signals in one embodiment comprise the electrocardiogram, blood oxygen, blood pressure, body temperature, etc., and the physiological parameter signals are generally measured and obtained by means of sensors, etc., and a plurality of physiological parameter signals may be signals of the same type or different types. Each of the physiological parameter signals is separately analyzed, so as to obtain a feature of each of the physiological parameter signals. Each of the physiological parameter signals has its respective feature, and the analysis of a single signal herein may be performed by using a solution in the prior art.

Step S102, obtaining a fusion state of the at least two physiological parameter signals according to the features of the at least two physiological parameter signals.

A fusion state of a plurality of physiological parameter signals includes a fusion of the at least two physiological parameter signals with a first physiological parameter signal is dominant, and a fusion of the at least two physiological parameter signals with a second physiological parameter signal is dominant, and thus it may be determined that the plurality of physiological parameter signals may be fused, and it may be determined as regards which of the physiological parameter signals is dominant. Here, "first" and "second" are not specifically indicated, have no special meanings, and also do not represent a sequential relationship. The analysis can also be performed on more than three physiological parameter signals so as to obtain a fusion state of the more than three physiological parameter signals, and at this time, one or two of the physiological parameter signals may be dominate. When one or several of the plurality of physiological parameter signals is(are) dominant, it may be indicated that a feature, such as Single Quality Index(es) (SQI) of the physiological parameter signal(s) is(are) good, and it may be also indicated that the physiological parameter signal(s) has(have) the other advantageous features.

Step S103, outputting the fusion state of the at least two physiological parameter signals, the outputting including:

if the fusion state is the fusion of the at least two physiological parameter signals with the first physiological parameter signal is dominant, highlighting the first physiological parameter signal, and if the fusion state is the fusion of the at least two physiological parameter signals with the second physiological parameter signal is dominant, highlighting the second physiological parameter signal;

outputting the fusion state of the at least two physiological parameter signals, the outputting including: highlighting, if the fusion state is the fusion of the at least two physiological parameter signals with the first physiological parameter signal is dominant, the first physiological parameter signal, and highlighting, if the fusion state is the fusion of the at least two physiological parameter signals with the second physiological parameter signal is dominant, the second physiological parameter signal, such that a joint determination mechanism among various physiological parameters is solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and making it possible to easily and rapidly determine the change in key physiological information about a patient.

Specifically, the physiological parameter signal which is dominant may be highlighted by means of a color, a graphic or a set identifier, or a combination of the two or three above.

According to the physiological parameter signal fusion processing method provided in the embodiments of the present disclosure, by means of respectively analyzing at least two input physiological parameter signals to obtain a feature of each of the physiological parameter signals, obtaining and outputting a fusion state of the at least two physiological parameter signals according to the feature of each of the physiological parameter signals, highlighting, if the fusion state is the fusion of the at least two physiological parameter signals with the first physiological parameter signal is dominant, the first physiological parameter signal, and highlighting, if the fusion state is the fusion of the at least two physiological parameter signals with the second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient.

Figure 2:
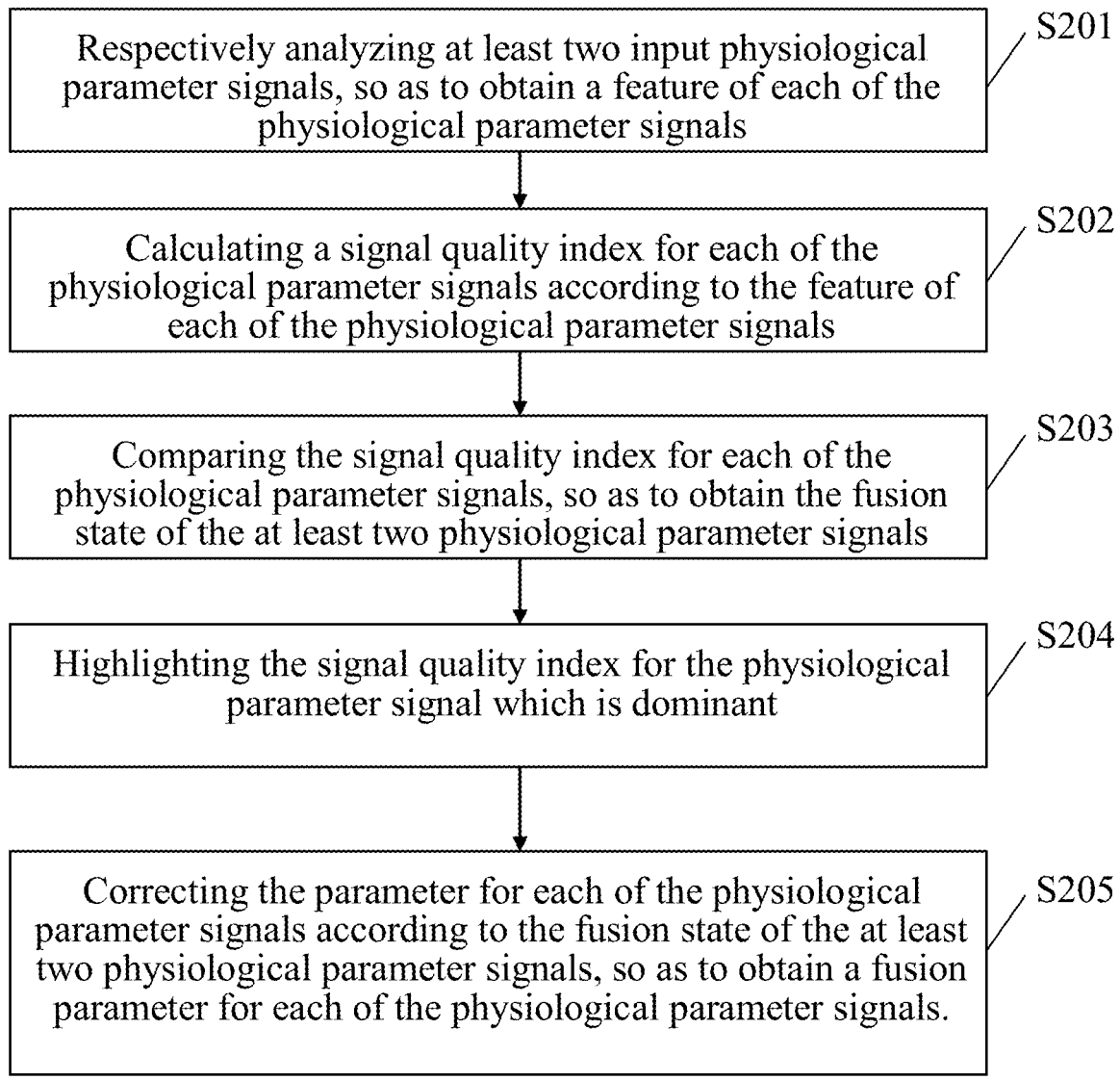
FIG. 2 is a schematic flow diagram of another physiological parameter signal fusion processing method.

FIG. 2 is a schematic flow diagram of another physiological parameter signal fusion processing method provided in the embodiments of the present disclosure, the method including the steps of:

S201, respectively analyzing at least two input physiological parameter signals, so as to obtain a feature of each of the physiological parameter signals.

Each of the physiological parameter signals is separately analyzed, so as to obtain a feature of each of the physiological parameter signals. Specifically, pre-processing such as high-pass and low-pass filtering may be first performed on each of the physiological parameter signals so as to filter high-frequency noise and baseline drifts, and then a feature of each of the physiological parameter signals may be extracted.

S202, calculating a signal quality index and a parameter for each of the physiological parameter signals according to the feature of each of the physiological parameter signals.

The signal quality index and the parameter for each of the physiological parameter signals may be obtained by means of calculating separately from the features of the physiological parameter signals. The feature and the parameter for each of the physiological parameter signals may be different, and the meaning of the feature and the parameter for the physiological parameter signal may be determined according to the prior art.

S203, comparing the signal quality index for each of the physiological parameter signals, so as to obtain the fusion state of the at least two physiological parameter signals.

The signal quality index is an important one of the features of the physiological parameter signals. Therefore, in one embodiment, the signal quality indexes calculated from the features of the plurality of physiological parameter signals may be compared to obtain a fusion state of the plurality of physiological parameter signals, so as to reflect the signal quality of each of the physiological parameter signals in the fusion process of the plurality of physiological parameter signals, and the physiological parameter signal with a better signal quality is determined as the dominant physiological parameter signal.

S204, highlighting the signal quality index for the physiological parameter signal which is dominant.

In this step, the signal quality indexes of the plurality of physiological parameter signals are displayed, and the signal quality index for the dominant physiological parameter signal is highlighted by means of a color, an image or a set identifier, or a combination of any two above or a combination of three above. By means of a signal quality graph, a user may be prompted, to a certain extent, to adjust a connection or use state of a sensor, so as to improve the poor signal quality of the physiological parameter signal.

Figure 7:
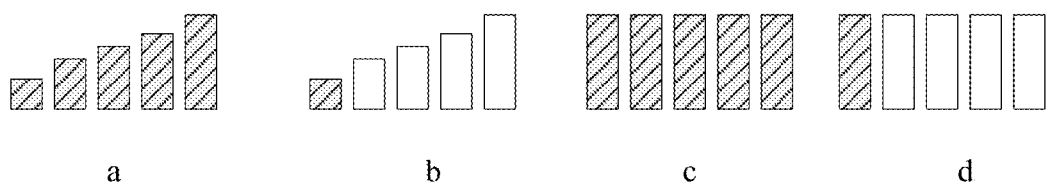
FIG. 7 is a schematic diagram of an exemplary signal quality.

FIG. 7 is a schematic diagram of an exemplary signal quality, which may be displayed using a signal square lattice graph in an ascending shape, and may also be displayed using a parallel square graph as shown in a and b in FIG. 7, and the square graph can also be correspondingly rotated, which is not limited here. When the signal quality is the strongest, the shadow in the square lattice is full, and when the signal is weak, the number of shaded square lattices is reduced in sequence. The signal quality graph may also be a traffic signal graph or is represented by identifying the background of a physiological parameter signal graph itself with a set color, which will be described in detail in the following variation solution.

Figure 8:
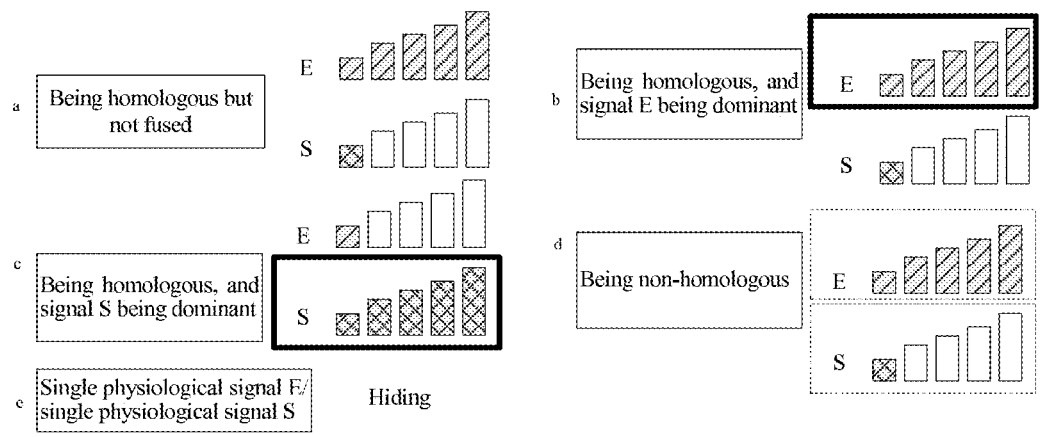
FIG. 8 is a schematic diagram of an exemplary state synthesis result.

FIG. 8 is a schematic diagram of an exemplary state synthesis result. An identifier, for example, "E" and "S", of a physiological parameter signal is labeled beside the signal quality graph, and shadows of the square lattice in the signal quality graph of different physiological parameter signals are different. Certainly, the shape of the shadows can also be replaced by different colors. In a schematic diagram of the state synthesis result, FIGS. b and c embody schematic diagrams of the fusion state therein. As shown in FIG. b of FIG. 8, which indicates being homologous and signal E being dominant, a solid-line box is used to outline the signal quality graph of signal E. As shown in FIG. c of FIG. 8, which indicates being homologous and signal S being dominant, a solid-line box is used to outline the signal quality graph of signal S.

S205, correcting the parameter for each of the physiological parameter signals according to the fusion state of the at least two physiological parameter signals, so as to obtain a fusion parameter for each of the physiological parameter signals.

By means of fusing the plurality of physiological parameter signals, the fusion state thereof is obtained. In one embodiment, the fusion state embodies the signal quality of the plurality of physiological parameter signals. Therefore, the parameter for each of the physiological parameter signals is corrected according to the fusion state, so as to obtain the fusion parameter for each of the physiological parameter signals, such that the fusion parameter more realistically reflects the physiological condition of a patient.

According to the physiological parameter signal fusion processing method provided in the embodiments of the present disclosure, by means of respectively analyzing at least two input physiological parameter signals to obtain a feature of each of the physiological parameter signals, obtaining and outputting a fusion state of the at least two physiological parameter signals according to the feature of each of the physiological parameter signals, highlighting, if the fusion state is the fusion of the at least two physiological parameter signals with the first physiological parameter signal is dominant, the first physiological parameter signal, and highlighting, if the fusion state is the fusion of the at least two physiological parameter signals with the second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient. In addition, the parameter for each of the physiological parameter signals may be corrected according to the fusion state. In addition, by means of a signal quality graph, a user may be prompted, to a certain extent, to adjust a connection or use state of a sensor, so as to improve the poor signal quality of the physiological parameter signal.

Figure 3:
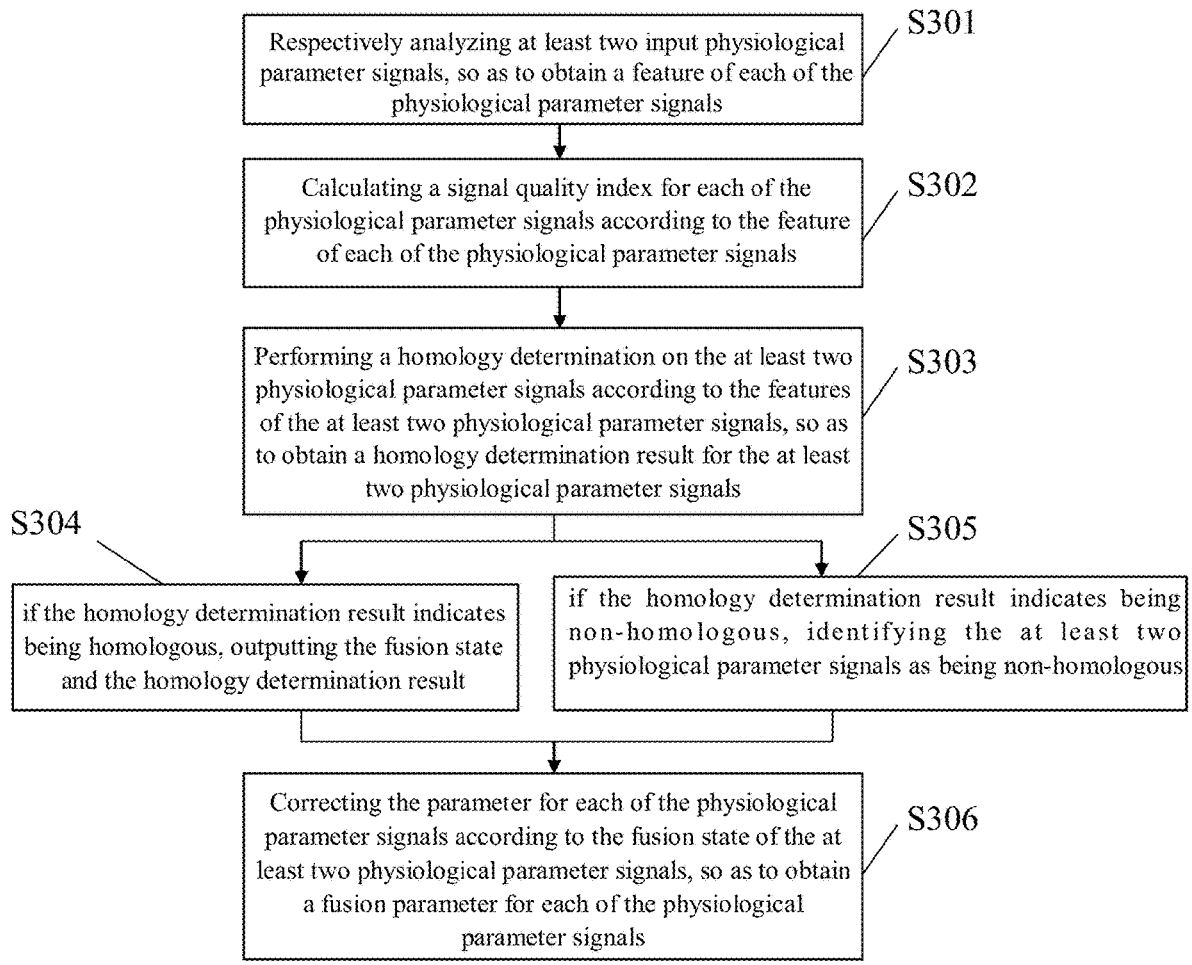
FIG. 3 is a schematic flow diagram of yet another physiological parameter signal fusion processing method.

FIG. 3 is a schematic flow diagram of yet another physiological parameter signal fusion processing method provided in the embodiments of the present disclosure, the method including the steps of:

S301, respectively analyzing at least two input physiological parameter signals, so as to obtain a feature of each of the physiological parameter signals.

Each of the physiological parameter signals is separately analyzed, so as to obtain a feature of each of the physiological parameter signals. Specifically, pre-processing such as high-pass and low-pass filtering may be first performed on each of the physiological parameter signals so as to filter high-frequency noise and baseline drifts, and then a feature of each of the physiological parameter signals may be extracted.

S302, calculating a signal quality index and a parameter for each of the physiological parameter signals according to the feature of each of the physiological parameter signals.

The signal quality index and the parameter for each of the physiological parameter signals may be obtained by means of calculating separately from the features of the physiological parameter signals. The feature and the parameter for each of the physiological parameter signals may be different, and the meaning of the feature and the parameter for the physiological parameter signal may be determined according to the prior art.

S303, performing a homology determination on the at least two physiological parameter signals according to the features of the at least two physiological parameter signals, so as to obtain a homology determination result for the at least two physiological parameter signals.

A feature of each of the plurality of physiological parameter signals is input for performing a homology determination on the plurality of physiological parameter signals, so as to obtain a homology determination result for the plurality of physiological parameter signals. The homology determination result includes: being homologous and non-homologous.

S304, if the homology determination result indicates being homologous, outputting the fusion state and the homology determination result.

S305, if the homology determination result indicates being non-homologous, identifying the at least two physiological parameter signals as being non-homologous.

According to the homology determination result and the fusion state, several states may be divided as follows:

being homologous but not fused: which indicates that a plurality of parameter signals involved in the analysis come from the same individual but cannot be fused due to certain reasons;

being homologous, and physiological signal I being dominant: which indicates that a plurality of parameter signals involved in the analysis come from the same individual, and a feature of physiological parameter signal I is used to fuse with parameter results for physiological parameter signal II;

being homologous, and physiological signal II being dominant: which indicates that a plurality of parameter signals involved in the analysis come from the same individual, and a feature of physiological parameter signal II is used to fuse with parameter results for physiological parameter signal I;

being non-homologous; which indicates that a plurality of parameter signals involved in the analysis come from different individuals;

single physiological signal: which indicates that there is only one physiological parameter signal currently.

The fusion state and homology determination result above can both be identified in different manners on the basis of the signal quality index for the physiological parameter signal.

FIG. 7 is a schematic diagram of an exemplary signal quality, which may be displayed using a signal square lattice graph in an ascending shape, and may also be displayed using a parallel square graph as shown in a and b in FIG. 7, and the square graph can also be correspondingly rotated, which is not limited here. When the signal quality is the strongest, the shadow in the square lattice is full, and when the signal is weak, the number of shaded square lattices is reduced in sequence. The signal quality graph may also be a traffic signal graph or is represented by identifying the background of a physiological parameter signal graph itself with a set color, which will be described in detail in the following variation solution. It should be noted that the signal quality index and the state synthesis result may be output in a combined manner, and can also be output respectively.

FIG. 8 is a schematic diagram of an exemplary state synthesis result. An identifier, for example, "E" and "S", of a physiological parameter signal is labeled beside the signal quality graph, and shadows of the square lattice in the signal quality graph of different physiological parameter signals are different. Certainly, the shape of the shadows can also be replaced by different colors. As shown in FIG. b of FIG. 8, which indicates being homologous and signal E being dominant, a solid-line box is used to outline the signal quality graph of signal E. As shown in FIG. c of FIG. 8, which indicates being homologous and signal S being dominant, a solid-line box is used to outline the signal quality graph of signal S. As shown in FIG. d of FIG. 8, which indicates that the two signals are non-homologous, a dotted-line box is used to outline both of the signal quality graphs of signals E and S. As shown in FIG. e of FIG. 8, which indicates a single-physiological signal state, displaying is not performed.

S306, correcting the parameter for each of the physiological parameter signals according to the fusion state of the at least two physiological parameter signals, so as to obtain a fusion parameter for each of the physiological parameter signals.

The parameter for and the fusion state of each of the physiological parameter signals are input for parameter merging, so as to respectively obtain the fusion parameter for each of the physiological parameter signals. In one embodiment, the fusion state obtained according to the signal quality indexes of the plurality of physiological parameter signals embodies the signal quality of the plurality of physiological parameter signals. Therefore, the parameter for each of the physiological parameter signals is corrected according to the fusion state, so as to obtain the fusion parameter for each of the physiological parameter signals, such that the fusion parameter more realistically reflects the physiological condition of a patient.

It may be seen from the above that the SQI embodies the reliability of multi-parameter fusion, the fusion state is used for presenting a result source of the multi-parameter fusion, and the fusion parameter for each of the physiological parameter signals is used for representing a fusion parameter analysis result.

According to the physiological parameter fusion processing method provided in the embodiments of the present disclosure, by means of performing state synthesis on the signal quality indexes of the plurality of physiological parameter signals and the homology determination result for the plurality of physiological parameter signals, obtaining a state synthesis result for the plurality of physiological parameter signals, and outputting the state synthesis result, and correcting the parameter for each of the physiological parameter signals according to the parameter for each of the physiological parameter signals and the state synthesis result, so as to obtain the fusion parameter for each of the physiological parameter signals, a joint judgment mechanism among various physiological parameters may be solved, and the state synthesis result can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient. In addition, the homology of the physiological parameter signals may be learnt; In addition, the parameter for each of the physiological parameter signals may be corrected according to the state fusion result. In addition, by means of a signal quality graph, a user may be prompted, to a certain extent, to adjust a connection or use state of a sensor, so as to improve the poor signal quality of the physiological parameter signal.

It should be noted that, for the sake of simple description, the foregoing method embodiments are all expressed as a series of action combinations, but those skilled in the art should understand that the present disclosure is not limited by the described action sequence, because certain steps may be performed in other sequences or concurrently in accordance with the present disclosure. Secondly, those skilled in the art should also understand that the embodiments described in the description are all preferred embodiments, and the actions and units involved therein are not necessarily required by the present disclosure.

Figure 4:
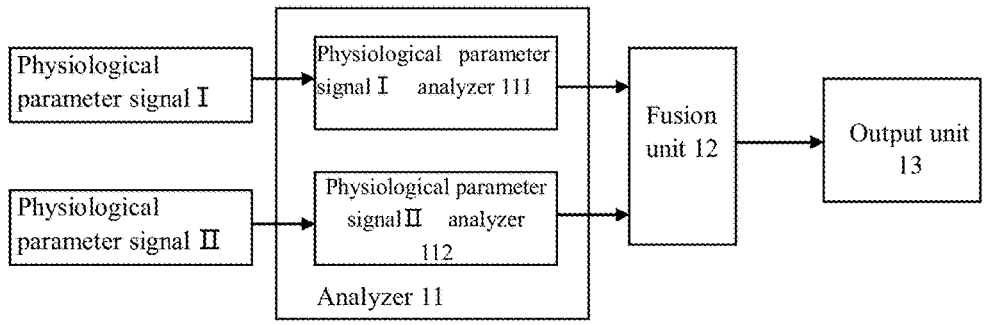
FIG. 4 is a structural schematic diagram of a physiological parameter signal fusion processing apparatus.

FIG. 4 is a structural schematic diagram of a physiological parameter signal fusion processing apparatus provided in the embodiments of the present disclosure, the apparatus including:

an analyzer 11 for respectively analyzing at least two input physiological parameter signals, so as to obtain a feature of each of the physiological parameter signals.

The physiological parameter signals in one embodiment comprise the electrocardiogram, blood oxygen, blood pressure, body temperature, etc., and the physiological parameter signals are generally measured and obtained by means of sensors, etc., and a plurality of physiological parameter signals may be signals of the same type or different types. Each of the physiological parameter signals is separately analyzed, so as to obtain a feature of each of the physiological parameter signals. Each of the physiological parameter signals has its respective feature, and the analysis of a single signal herein may be performed by using a solution in the prior art.

In FIG. 4, illustration is given using two physiological parameter signals as an example: physiological parameter signal I and physiological parameter signal II. Therefore, the analyzer 11 includes a physiological signal I analyzer 111 and a physiological signal II analyzer 112.

A fusion unit 12 for obtaining a fusion state of the at least two physiological parameter signals according to the features of the at least two physiological parameter signals.

A fusion state of a plurality of physiological parameter signals includes a fusion of the at least two physiological parameter signals with a first physiological parameter signal is dominant, and a fusion of the at least two physiological parameter signals with a second physiological parameter signal is dominant, and thus it may be determined that the plurality of physiological parameter signals may be fused, and it may be determined as regards which of the physiological parameter signals is dominant. Here, "first" and "second" are not specifically indicated, have no special meanings, and also do not represent a sequential relationship. The analysis can also be performed on more than three physiological parameter signals so as to obtain a fusion state of the more than three physiological parameter signals, and at this time, one or two of the physiological parameter signals may be dominate. When one or several of the plurality of physiological parameter signals is(are) dominant, it may be indicated that a feature, such as Single Quality Index(es) (SQI) of the physiological parameter signal(s) is(are) good, and it may be also indicated that the physiological parameter signal(s) has(have) the other advantageous features.

An output unit 13 for outputting the fusion state of the at least two physiological parameter signals, the outputting including: if the fusion state is the fusion of the at least two physiological parameter signals with the first physiological parameter signal is dominant, highlighting the first physiological parameter signal, and if the fusion state is the fusion of the at least two physiological parameter signals with the second physiological parameter signal is dominant, highlighting the second physiological parameter signal.

outputting the fusion state of the at least two physiological parameter signals, the outputting including: highlighting, if the fusion state is the fusion of the at least two physiological parameter signals with the first physiological parameter signal is dominant, the first physiological parameter signal, and highlighting, if the fusion state is the fusion of the at least two physiological parameter signals with the second physiological parameter signal is dominant, the second physiological parameter signal, such that a joint determination mechanism among various physiological parameters is solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and making it possible to easily and rapidly determine the change in key physiological information about a patient.

Specifically, the physiological parameter signal which is dominant may be highlighted by means of a color, a graphic or a set identifier, or a combination of the two or three above.

According to the physiological parameter signal fusion processing apparatus provided in the embodiments of the present disclosure, by means of respectively analyzing at least two input physiological parameter signals to obtain a feature of each of the physiological parameter signals, obtaining and outputting a fusion state of the at least two physiological parameter signals according to the feature of each of the physiological parameter signals, highlighting, if the fusion state is a fusion of the at least two physiological parameter signals with a first physiological parameter signal is dominant, the first physiological parameter signal, and highlighting, if the fusion state is a fusion of the at least two physiological parameter signals with a second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient.

Figure 5A:
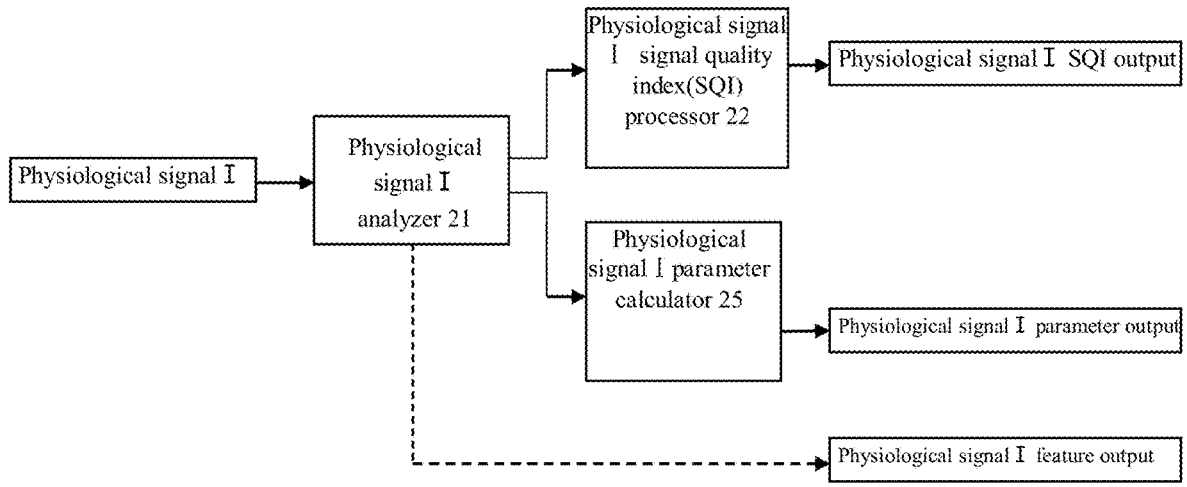
FIGS. 5A and 5B are structural schematic diagrams of another physiological parameter signal fusion processing apparatus.
Figure 5B:
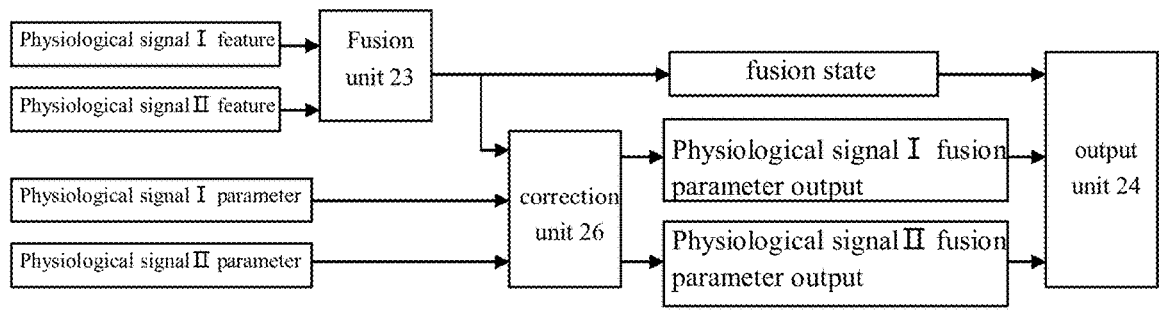

FIGS. 5A and 5B are structural schematic diagrams of another physiological parameter signal fusion processing apparatus provided in the embodiments of the present disclosure, the apparatus including:

an analyzer 21 for respectively analyzing at least two input physiological parameter signals, so as to obtain a feature of each of the physiological parameter signals.

Each of the physiological parameter signals is separately analyzed, so as to obtain a feature of each of the physiological parameter signals. Specifically, pre-processing such as high-pass and low-pass filtering may be first performed on each of the physiological parameter signals so as to filter high-frequency noise and baseline drifts, and then a feature of each of the physiological parameter signals may be extracted.

FIG. 5A is a block diagram of processing physiological parameter signal I before fusing. The processing of the other physiological parameter signals is similar.

A signal processor 22 for calculating a signal quality index for each of the physiological parameter signals according to the feature of each of the physiological parameter signals.

The signal quality index and the parameter for each of the physiological parameter signals may be obtained by means of calculating separately from the features of the physiological parameter signals. The feature and the parameter for each of the physiological parameter signals may be different, and the meaning of the feature and the parameter for the physiological parameter signal may be determined according to the prior art.

A fusion unit 23 for comparing the signal quality index for each of the physiological parameter signals, so as to obtain the fusion state of the at least two physiological parameter signals.

The signal quality index is an important one of the features of the physiological parameter signals. Therefore, in one embodiment, the signal quality indexes calculated from the features of the plurality of physiological parameter signals may be compared to obtain a fusion state of the plurality of physiological parameter signals, so as to reflect the signal quality of each of the physiological parameter signals in the fusion process of the plurality of physiological parameter signals, and the physiological parameter signal with a better signal quality is determined as the dominant physiological parameter signal.

An output unit 24 for highlighting the signal quality index for the dominant physiological parameter signal.

The signal quality indexes of the plurality of physiological parameter signals are displayed, and the signal quality index for the dominant physiological parameter signal is highlighted by means of a color, an image or a set identifier, or a combination of any two above or a combination of three above. By means of a signal quality graph, a user may be prompted, to a certain extent, to adjust a connection or use state of a sensor, so as to improve the poor signal quality of the physiological parameter signal.

FIG. 7 is a schematic diagram of an exemplary signal quality, which may be displayed using a signal square lattice graph in an ascending shape, and may also be displayed using a parallel square graph as shown in a and b in FIG. 7, and the square graph can also be correspondingly rotated, which is not limited here. When the signal quality is the strongest, the shadow in the square lattice is full, and when the signal is weak, the number of shaded square lattices is reduced in sequence. The signal quality graph may also be a traffic signal graph or is represented by identifying the background of a physiological parameter signal graph itself with a set color, which will be described in detail in the following variation solution.

FIG. 8 is a schematic diagram of an exemplary state synthesis result. An identifier, for example, "E" and "S", of a physiological parameter signal is labeled beside the signal quality graph, and shadows of the square lattice in the signal quality graph of different physiological parameter signals are different. Certainly, the shape of the shadows can also be replaced by different colors. In a schematic diagram of the state synthesis result, views b and c embody a schematic diagram of the fusion state therein. As shown in view b of FIG. 8, which indicates being homologous and signal E being dominant, a solid-line box is used to outline the signal quality graph of signal E. As shown in view c of FIG. 8, which indicates being homologous and signal S being dominant, a solid-line box is used to outline the signal quality graph of signal S.

A parameter calculator 25 for calculating a parameter for each of the physiological parameter signals according to the feature of each of the physiological parameter signals.

A correction unit 26 for correcting the parameter for each of the physiological parameter signals according to the fusion state of the at least two physiological parameter signals, so as to obtain a fusion parameter for each of the physiological parameter signals.

By means of fusing the plurality of physiological parameter signals, the fusion state thereof is obtained. In one embodiment, the fusion state embodies the signal quality of the plurality of physiological parameter signals. Therefore, the parameter for each of the physiological parameter signals is corrected according to the fusion state, so as to obtain the fusion parameter for each of the physiological parameter signals, such that the fusion parameter is improved in signal quality.

According to the physiological parameter signal fusion processing apparatus provided in the embodiments of the present disclosure, by means of respectively analyzing at least two input physiological parameter signals to obtain a feature of each of the physiological parameter signals, obtaining and outputting a fusion state of the at least two physiological parameter signals according to the feature of each of the physiological parameter signals, highlighting, if the fusion state is a fusion of the at least two physiological parameter signals with a first physiological parameter signal is dominant, the first physiological parameter signal, and highlighting, if the fusion state is a fusion of the at least two physiological parameter signals with a second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient. In addition, the parameter for each of the physiological parameter signals may be corrected according to the fusion state. In addition, by means of a signal quality graph, a user may be prompted, to a certain extent, to adjust a connection or use state of a sensor, so as to improve the poor signal quality of the physiological parameter signal.

Figure 6:
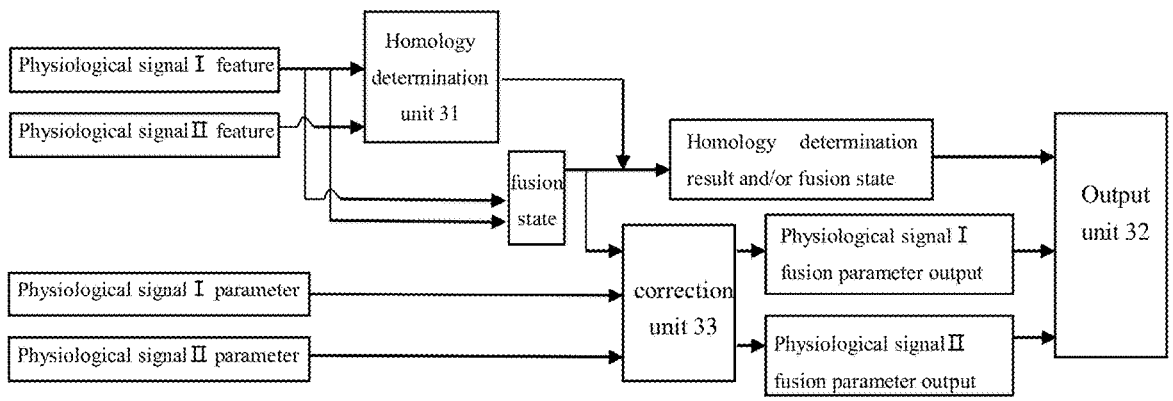
FIG. 6 is a structural schematic diagram of yet another physiological parameter signal fusion processing apparatus.

FIG. 6 is a structural schematic diagram of yet another physiological parameter signal fusion processing apparatus provided in the embodiments of the present disclosure, the apparatus including:

an analyzer for respectively analyzing at least two input physiological parameter signals, so as to obtain a feature of each of the physiological parameter signals.

Each of the physiological parameter signals is separately analyzed, so as to obtain a feature of each of the physiological parameter signals. Specifically, pre-processing such as high-pass and low-pass filtering may be first performed on each of the physiological parameter signals so as to filter high-frequency noise and baseline drifts, and then a feature of each of the physiological parameter signals may be extracted.

A signal processor for calculating a signal quality index for each of the physiological parameter signals according to the feature of each of the physiological parameter signals.

The signal quality index and the parameter for each of the physiological parameter signals may be obtained by means of calculating separately from the features of the physiological parameter signals. The feature and the parameter for each of the physiological parameter signals may be different, and the meaning of the feature and the parameter for the physiological parameter signal may be determined according to the prior art.

The feature extraction, signal quality index calculation and parameter calculation for the physiological parameter signal are the same as those in the foregoing embodiments, and will not embodied again in FIG. 6.

A homology determination unit 31 for performing a homology determination on the at least two physiological parameter signals according to the features of the at least two physiological parameter signals, so as to obtain a homology determination result for the at least two physiological parameter signals.

A feature of each of the plurality of physiological parameter signals is input for performing a homology determination on the plurality of physiological parameter signals, so as to obtain a homology determination result for the plurality of physiological parameter signals. The homology determination result includes: being homologous and non-homologous.

An output unit 32 for outputting, if the homology determination result indicates being homologous, the fusion state and the homology determination result.

The output unit 32 is further used for identifying, if the homology determination result indicates being non-homologous, the at least two physiological parameter signals as being non-homologous.

According to the homology determination result and the fusion state, several states may be divided as follows:

being homologous but not fused: which indicates that a plurality of parameter signals involved in the analysis come from the same individual but cannot be fused due to certain reasons;

being homologous, and physiological signal I being dominant: which indicates that a plurality of parameter signals involved in the analysis come from the same individual, and a feature of physiological parameter signal I is used to fuse with parameter results for physiological parameter signal II;

being homologous, and physiological signal II being dominant: which indicates that a plurality of parameter signals involved in the analysis come from the same individual, and a feature of physiological parameter signal II is used to fuse with parameter results for physiological parameter signal I;

being non-homologous; which indicates that a plurality of parameter signals involved in the analysis come from different individuals;

single physiological signal: which indicates that there is only one physiological parameter signal currently.

The fusion state and homology determination result above can both be identified in different manners on the basis of the signal quality index for the physiological parameter signal.

FIG. 7 is a schematic diagram of an exemplary signal quality, which may be displayed using a signal square lattice graph in an ascending shape, and may also be displayed using a parallel square graph as shown in views a and b in FIG. 7, and the square graph can also be correspondingly rotated, which is not limited here. When the signal quality is the strongest, the shadow in the square lattice is full, and when the signal is weak, the number of shaded square lattices is reduced in sequence. The signal quality graph may also be a traffic signal graph or is represented by identifying the background of a physiological parameter signal graph itself with a set color, which will be described in detail in the following variation solution. It should be noted that the signal quality index and the state synthesis result may be output in a combined manner, and can also be output respectively.

FIG. 8 is a schematic diagram of an exemplary state synthesis result. An identifier, for example, "E" and "S", of a physiological parameter signal is labeled beside the signal quality graph, and shadows of the square lattice in the signal quality graph of different physiological parameter signals are different. Certainly, the shape of the shadows can also be replaced by different colors. As shown in FIG. b of FIG. 8, which indicates being homologous and signal E being dominant, a solid-line box is used to outline the signal quality graph of signal E. As shown in FIG. c of FIG. 8, which indicates being homologous and signal S being dominant, a solid-line box is used to outline the signal quality graph of signal S. As shown in FIG. d of FIG. 8, which indicates that the two signals are non-homologous, a dotted-line box is used to outline both of the signal quality graphs of signals E and S. As shown in FIG. e of FIG. 8, which indicates a single-physiological signal state, displaying is not performed.

A parameter calculator for calculating a parameter for each of the physiological parameter signals according to the feature of each of the physiological parameter signals.

A correction unit 33 for correcting the parameter for each of the physiological parameter signals according to the fusion state of the at least two physiological parameter signals may be provided, so as to obtain a fusion parameter for each of the physiological parameter signals.

The parameter for and the fusion state of each of the physiological parameter signals are input for parameter fusion, so as to respectively obtain the fusion parameter for each of the physiological parameter signals. In one embodiment, the fusion state obtained according to the signal quality indexes of the plurality of physiological parameter signals embodies the signal quality of the plurality of physiological parameter signals. Therefore, the parameter for each of the physiological parameter signals is corrected according to the fusion state, so as to obtain the fusion parameter for each of the physiological parameter signals, such that the fusion parameter more realistically reflects the physiological condition of a patient.

It may be seen from the above that the SQI embodies the reliability of multi-parameter fusion, the fusion state is used for presenting a result source of the multi-parameter fusion, and the fusion parameter for each of the physiological parameter signals is used for representing a fusion parameter analysis result.

According to the physiological parameter fusion processing apparatus provided in the embodiments of the present disclosure, by means of performing state synthesis on the signal quality indexes of the plurality of physiological parameter signals and the homology determination result for the plurality of physiological parameter signals, obtaining a state synthesis result for the plurality of physiological parameter signals, and outputting the state synthesis result, and correcting the parameter for each of the physiological parameter signals according to the parameter for each of the physiological parameter signals and the state synthesis result, so as to obtain the fusion parameter for each of the physiological parameter signals, a joint judgment mechanism among various physiological parameters may be solved, and the state synthesis result can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient. In addition, the homology of the physiological parameter signals may be learnt; In addition, the parameter for each of the physiological parameter signals may be corrected according to the state fusion result. In addition, by means of a signal quality graph, a user may be prompted, to a certain extent, to adjust a connection or use state of a sensor, so as to improve the poor signal quality of the physiological parameter signal.

Figure 9:
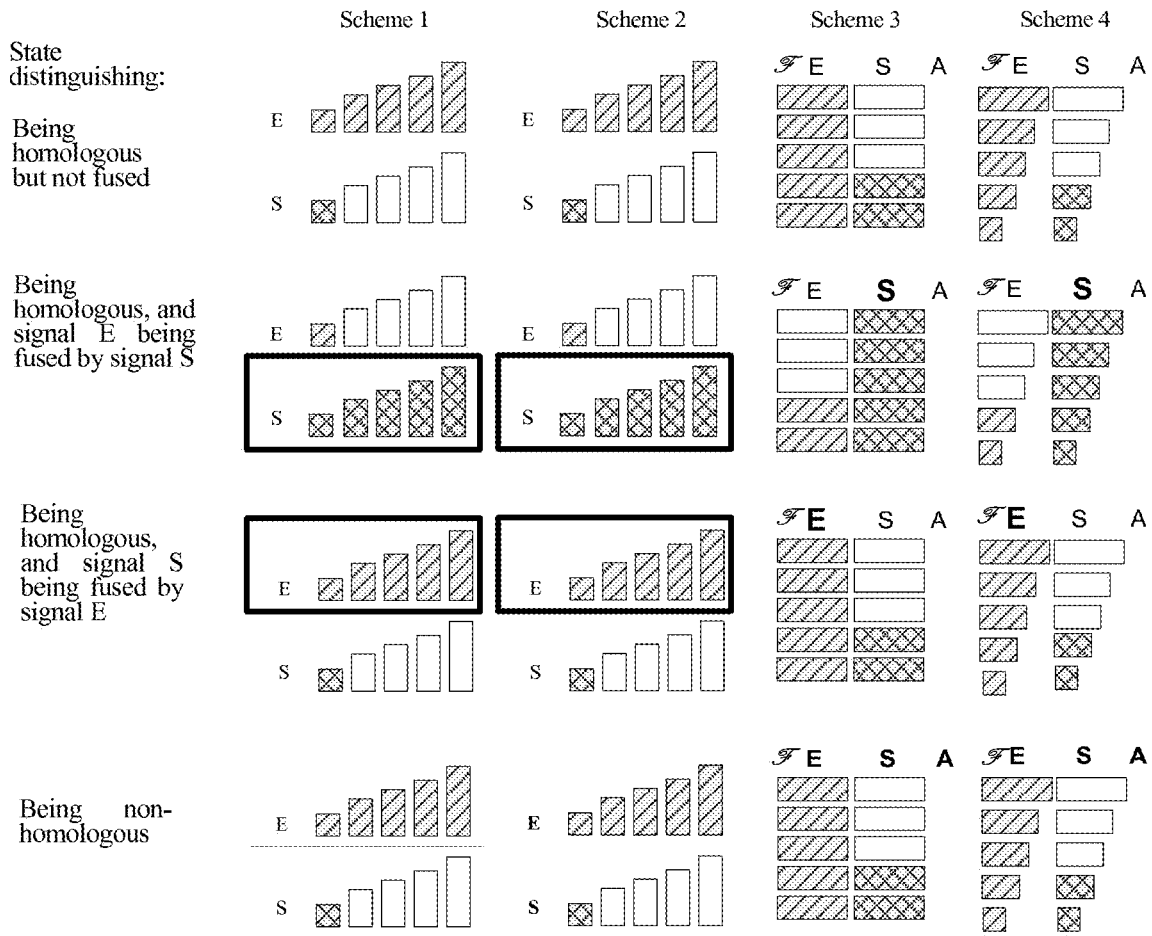
FIG. 9 is a schematic diagram of another exemplary state synthesis result.

Several alternative ways of displaying the state synthesis result are described below. As another implementation, FIG. 9 is a schematic diagram of another exemplary state synthesis result. Compared with the presentation of the fusion analysis state result in FIG. 8, FIG. 9 includes four slightly deformed presentation schemes. For example, in scheme 1, if the two parameter signals are non-homologous, an underline is added to the signal quality graph of the two parameter signals to replace the dotted-line box in FIG. 8. For example, in scheme 2, if the two parameter signals are non-homologous, the identifiers of the two parameter signals are highlighted, for example in a bold or large-font manner. For example, in scheme 3, an identifier, such as "𝓕 ESA" is used to represent a fusion state. If the state indicates being homologous but not fused, the identifier is normally displayed; if the state indicates being homologous and signal E being merged by signal S, i.e. signal S being dominant, "S" in the identifier is highlighted; likewise, if the state indicates being homologous and signal S being fused by signal E, i.e. signal E being dominant, "E" in the identifier is highlighted; and if the state indicates being non-homologous as shown in the figure, the entire identifier is highlighted, and is not displayed if the state indicates being single signal. Scheme 4 is the same as scheme 3, except that the square lattices of the signal quality graphs of the two use different shapes. It should be noted that when a certain signal is dominant, an "𝓕 ESA" identifier may be distinguished by means of a color in addition to highlighting the identifier of the signal, for example, when the identifier is fully bright, it indicates being homologous but not fused; when an identifier corresponding to the signal quality graph is changed, it indicates that a signal corresponding to the identifier dominates fusion; and when the identifier becomes grey, it indicates being not fused.

Figure 10:
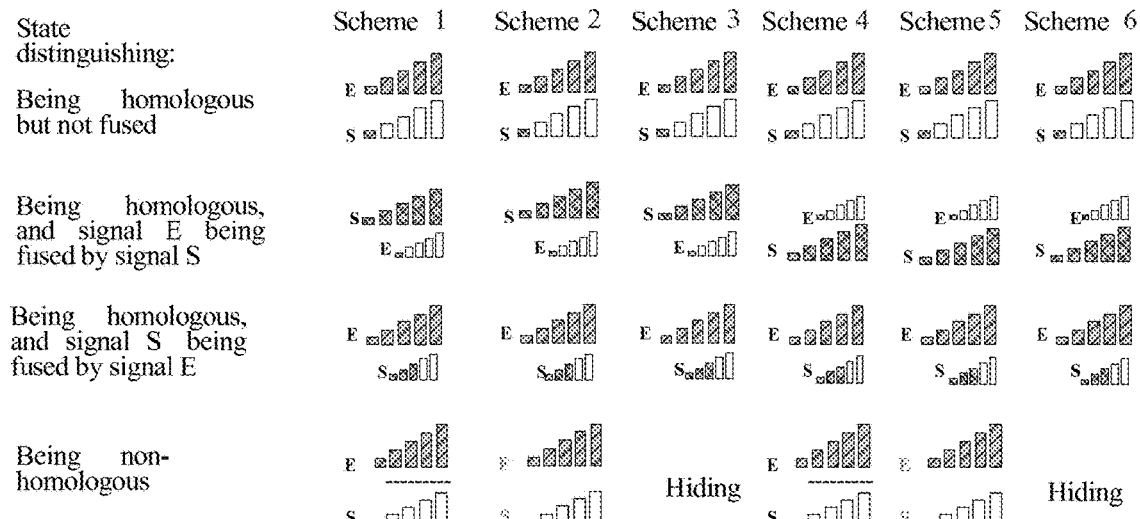
FIG. 10 is a schematic diagram of yet another exemplary state synthesis result.

As yet another alternative, FIG. 10 shows the schematic diagram of yet another state synthesis result. In the case of being homologous and signal A being fused by signal B, signal A and an identifier thereof may be reduced on the same scale, whereas signal B and an identifier thereof remain in the original size; in addition, the positions of signal quality graphs of signal A and signal B can also be exchanged (the original arrangement sequence of the signal quality graphs is successively signal quality graph A and signal quality graph B, and after exchange, the arrangement sequence is successively signal quality graph B and signal quality graph A). For the case of being non-homologous, distinguishing may be performed by hiding signals, and the method described above may also be used.

Figure 11:
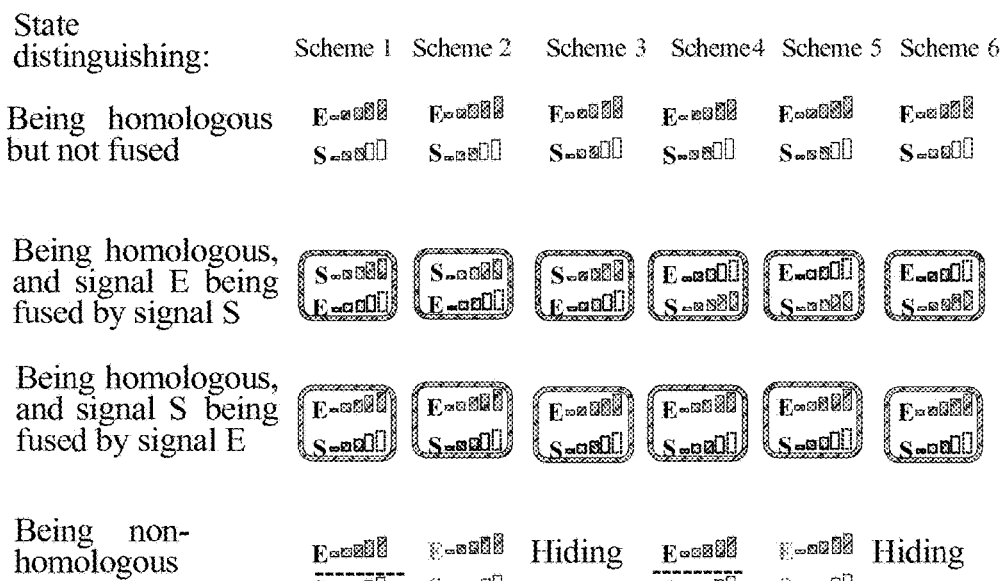
FIG. 11 is a schematic diagram of yet another exemplary state synthesis result.

As yet another alternative, FIG. 11 shows the schematic diagram of yet another state synthesis result output. In the case of being homologous and a certain signal being dominant, the identifiers and signal quality graphs of all signals are framed by a large box, and a solid line is used for the lines of a square lattice for a signal quality graph of the dominant signal, whereas a dotted line is used for the lines of a square lattice for a signal quality graph of a non-dominant signal. In addition, the positions of the signal quality graphs of the dominant signal and the non-dominant signal can also be exchanged.

As yet another alternative, FIG. 12 shows a schematic diagram of another signal quality index. In FIG. 12, the signal quality indexes are represented by means of traffic lights, in which R, Y, G and B respectively represent different colors, and different colors represent different signal qualities.

As yet another alternative, FIG. 13 is a schematic diagram of yet another state synthesis result. In FIG. 13, the signal quality indexes are represented by means of traffic lights, and when a certain signal is dominant, it is represented by a traffic light framed by a box; and for the case of being non-homologous or single-parameter signal, the signal quality index is represented by means of a signal becoming grey, adding an underline or adding a dotted box, or hiding, etc.

As yet another alternative, FIG. 14 is a schematic diagram of yet another state synthesis result, which differs from FIG. 13 in that, in FIG. 14, when a certain signal is dominant, the signal quality indexes are represented by means of traffic lights for all signals being framed by boxes, and the signal with the maximum signal quality index is dominant.

Figure 15:
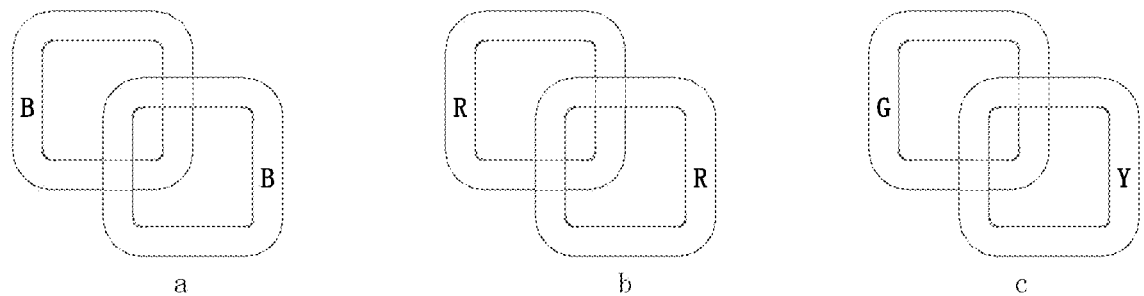
FIG. 15 is a schematic diagram of yet another exemplary state synthesis result.

As yet another alternative, FIG. 15 is a schematic diagram of yet another state synthesis result, in which a signal fusion process may also be only presented by means of an independent graph, but the signal quality is not embodied in the graph at the same time. For example, a fusion analysis state is simplified, homologous states are fused, no distinguishing is made for a dominant form. Thus, three states are divided for presentation, namely: being non-homologous/single parameter, being homologous and fused, and being homologous but not fused.

Figure 16:
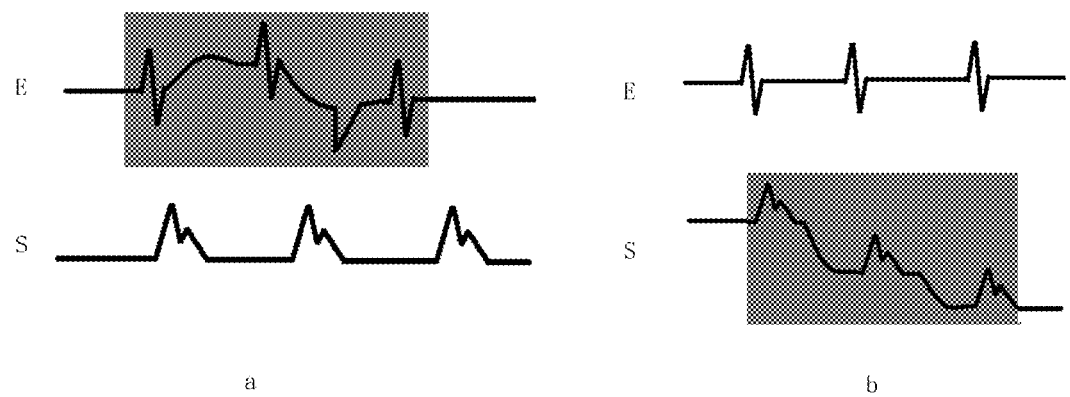
FIG. 16 is a schematic diagram of yet another exemplary state synthesis result.

As yet another alternative, FIG. 16 is a schematic diagram of yet another state synthesis result. In FIG. 16, the state synthesis result is separately presented from the signal quality index. When a certain signal has a good quality, the waveform background of the corresponding signal has no color, and if the signal quality is poor, the background is identified by one color. As shown in FIG. 16 (1), the signal quality of signal E in view a is poor, and the signal quality of signal S in view b is poor.

It should be noted that the above-mentioned representation manners of the signal quality graph and different state synthesis results may be cross-selected, and are not limited to the above-mentioned examples.

According to an independent analysis of each of the physiological parameter signals and a fusion analysis of the plurality of physiological parameter signals, a fusion analysis state of the plurality of physiological parameter signals, a fusion parameter for each of the physiological parameter signals and a signal quality index for each of the physiological parameter signals are output, so that a joint judgment mechanism among various physiological parameters may be solved, the false alarms caused by interfered single parameter measurement are reduced, the highlighting of key and reliable information is realized, and a user can intuitively learn a fusion process and a fusion result of the plurality of physiological parameter signals and the change in key physiological information about a patient may be easily and rapidly determined.

The fusion of the specific electrocardiogram (ECG) signal and blood oxygen (SPO2) signal is taken as an example for illustration below:

the electrocardiogram signal is physiological parameter signal I, and the blood oxygen signal is physiological parameter signal II; the ECG signal waveform is set to be green on a monitor interface, and the SPO2 signal waveform is set to be blue on the monitor interface; and in the following discussion, SPO2 is used to represent the blood oxygen signal and spo2 is used to represent the saturation of blood oxygen.

The fusion process may be as follows:
(1) performing single-signal analysis on an ECG signal by means of an ECG analyzer;
(2) performing single-signal analysis on an SPO2 signal by means of an SPO2 analyzer;
(3) feeding results in (1) and (2) into a fusion unit for fusion analysis; and
(4) presenting an output result in (3).

The specific flow of performing single-signal analysis on an ECG signal by means of an ECG analyzer may be as follows:
1) performing high-pass filtering on the ECG signal, for example, setting a cut-off frequency of the high-pass filtering to be 0.05 hz, and then performing low-pass filtering on same, for example, setting a cut-off frequency of the low-pass filtering to be 40 hz;
2) detecting and classifying QRS waves on the basis of the filtered signal, and calculating the SNR of the QRS waves;
3) calculating a corresponding ECGSQI by means of the SNR of the QRS waves;
4) calculating the HR of the ECG according to position information about the QRS waves, and analyzing the ARR of the ECG by means of the position information and classification information about the QRS waves; and
5) outputting QRS feature information.

The specific flow of performing single-signal analysis on an SPO2 signal by means of an SPO2 analyzer may be as follows:
1) performing high-pass filtering on the SPO2 signal, for example, setting a cut-off frequency of the high-pass filtering to be 0.3 hz, and then performing low-pass filtering on same, for example, setting a cut-off frequency of the low-pass filtering to be 5 hz;
2) detecting a PULSE wave on the basis of the filtered signal and calculating the SNR of the PULSE;
3) calculating a corresponding SPO2SQI by means of the SNR of the PULSE wave;
4) calculating the PR by means of position information about the PULSE wave, and estimating spo2 according to the ratio between an alternating-current component and a direct-current component of the PULSE wave; and
5) outputting PULSE feature.

The specific flow of feeding an independent analysis result of various physiological parameter signals into a fusion unit for fusion analysis may be as follows:
1) performing a homology determination on the QRS wave and the PULSE;
2) performing state synthesis according to a homology determination result, the ECGSQI and the SPO2SQI;
3) performing parameter fusing and outputting on HR/ARR and PR/spo2 according to the fusion state, so as to obtain fused HR/ARR and PR/spo2; and
4) outputting the fusion analysis state, the ECGSQI, the SPO2SQI, the fused HR/ARR and the fused PR/spo2 by means of a monitor.

What are displayed in the monitor comprise an electrocardiogram signal quality (ECGSQI), a blood oxygen signal quality (SPO2SQI), the fusion analysis state, the heart rate (HR) in electrocardiogram, an arrhythmia result (ARR), the pulse rate (PR) in blood oxygen, and saturation of blood oxygen (spo2). The classification of the fusion analysis states includes five states of: ECG and SPO2 being homologous but not fused; ECG and SPO2 being homologous, and ECG being dominant; ECG and SPO2 being homologous, and SPO2 being dominant; ECG and SPO2 being non-homologous; single ECG/single SPO2.

Specifically, the state of being homologous but not fused presented in the fusion analysis state graph indicates that ECG and SPO2 currently belong to different individuals, and fusing does not work; and the ECG signal quality fills 5 boxes in all signal quality graphs, indicating that the ECG signal quality is good, and the SPO2 signal quality fills only one box, indicating that the SPO2 signal quality is poor; or the state indicates that ECG and SPO2 belong to the same individual, indicating that the ECG signal quality is good, the blood oxygen signal is poor, the ECG dominates fusion, and a blood oxygen output result is fused by ECG; or the state indicates that ECG and SPO2 come from the same individual, indicating that the ECG signal quality is normal, the SPO2 signal quality is good, SPO2 dominates a fusion process, and an ECG output result is fused by SPO2; or the state indicates that ECG and SPO2 come from different individuals, indicating that the ECG signal quality is good, the SPO2 signal quality is poor, and an ECG output result and an SPO2 output result are not fused; or the state indicates single ECG/single SPO2, and a leads fail situation exists in the reason why this state occurs, and when this situation occurs, a corresponding position on the monitor interface is hidden.

Figure 17:
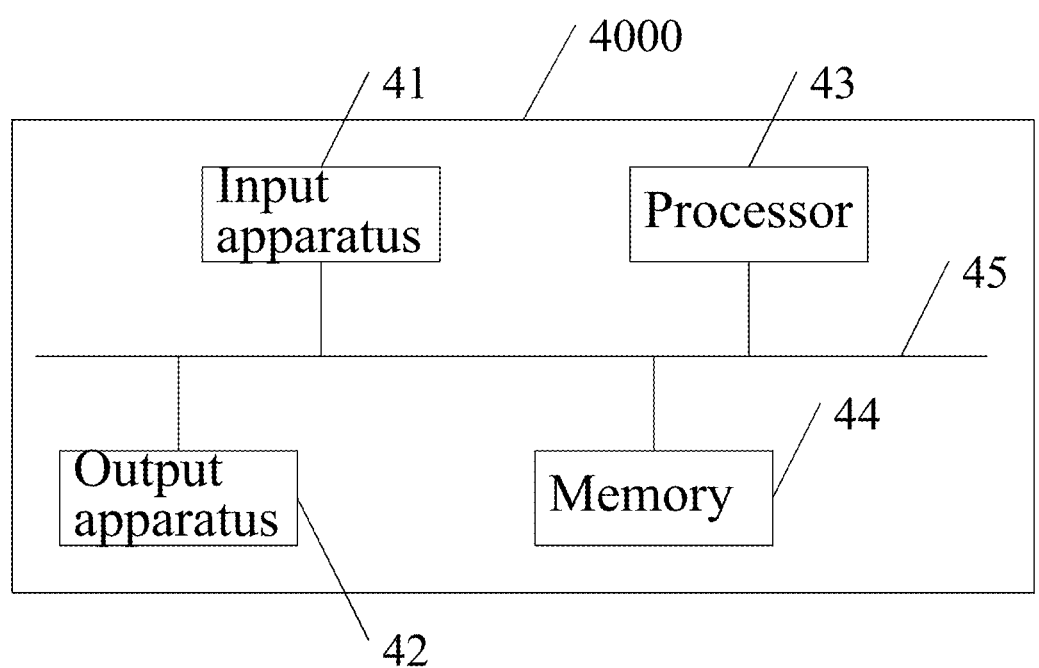
FIG. 17 is a structural schematic diagram of a physiological parameter signal fusion processing system.

FIG. 17 is a structural schematic diagram of a physiological parameter signal fusion processing system provided in the embodiments of the present disclosure for realizing the functions of the physiological parameter fusion processing. As shown in FIG. 17, the system 4000 includes an input apparatus 41, an output apparatus 42, a processor 43 and a memory 44, wherein the input apparatus 41, the output apparatus 42, the processor 43 and the memory 44 are connected to one another via a bus 45. The memory 44 stores a computer program, and the processor 43 executes the stored computer program, so that the system implements the above-mentioned physiological parameter fusion processing method.

The input apparatus 41 is used for inputting at least two physiological parameter signals.

The processor 43 is used for respectively analyzing at least two input physiological parameter signals, so as to obtain a feature of each of the physiological parameter signals.

The processor 43 is further used for obtaining a fusion state of the at least two physiological parameter signals according to the feature of each of the physiological parameter signals.

The output apparatus 42 is used for respectively outputting the fusion state of the at least two physiological parameter signals, the outputting including: if the fusion state is the fusion of the at least two physiological parameter signals with the first physiological parameter signal is dominant, highlighting the first physiological parameter signal, and if the fusion state is the fusion of the at least two physiological parameter signals with the second physiological parameter signal is dominant, highlighting the second physiological parameter signal.

As one implementation, the output apparatus 42 is specifically used for highlighting, by means of a color, a graphic and/or a set identifier, the dominant physiological parameter signal.

As another implementation, the processor 43 is specifically used for calculating a signal quality index for each of the physiological parameter signals according to the feature of each of the physiological parameter signals; and comparing the signal quality index for each of the physiological parameter signals, so as to obtain the fusion state of the at least two physiological parameter signals; and The output apparatus 42 is specifically used for highlighting the signal quality index for at least the physiological parameter signal which is dominant.

The signal quality index is represented by a background color set on a signal square lattice graph, a traffic signal graph or a physiological parameter signal waveform graph.

As yet another implementation, the processor 43 is further used for performing a homology determination on the at least two physiological parameter signals according to the features of the at least two physiological parameter signals, so as to obtain a homology determination result for the at least two physiological parameter signals, with the homology determination result including being homologous and non-homologous.

As yet another implementation, the output apparatus 42 is specifically used for outputting, if the homology determination result indicates being homologous, the fusion state and the homology determination result; and if the homology determination result indicates being non-homologous, identifying the at least two physiological parameter signals as being non-homologous.

As yet another implementation, the processor 43 is further used for:

calculating a parameter for each of the physiological parameter signals according to the feature of each of the physiological parameter signals; and correcting the parameter for each of the physiological parameter signals according to the fusion state of the at least two physiological parameter signals, so as to obtain a fusion parameter for each of the physiological parameter signals.

According to the physiological parameter fusion processing system provided in the embodiments of the present disclosure, by means of respectively analyzing a plurality of input physiological parameter signals to obtain a feature of each of the physiological parameter signals, obtaining and outputting a fusion state of the plurality of physiological parameter signals according to the feature of each of the physiological parameter signals, highlighting, if the fusion state is a fusion of the at least two physiological parameter signals with a first physiological parameter signal is dominant, the first physiological parameter signal, and highlighting, if the fusion state is a fusion of the at least two physiological parameter signals with a second physiological parameter signal is dominant, the second physiological parameter signal, a joint determination mechanism among various physiological parameters may be solved, and the fusion state can intuitively inform medical personnel of a measurement result source and that a parameter result of which kind of physiological parameter signals are more reliable and accurate, thereby reducing the false alarms caused by interfered single parameter measurement, realizing the highlighting of key and reliable information and helping doctors to easily and rapidly determine the change in key physiological information about a patient.

In the embodiments above, the various embodiments are described with their focuses, and with regard to a certain embodiment with parts not described in detail, reference may be made to the related descriptions of the other embodiments.

The steps in the method of the embodiments of the present disclosure may be sequentially adjusted, fused, and deleted according to actual needs.

The units in the apparatus of the embodiments of the present disclosure may be fused, divided, and deleted according to actual needs. Those skilled in the art can reconcile or combine different embodiments described in the description and the features of the different embodiments.

From the description of the embodiments above, those skilled in the art can clearly understand that the present disclosure may be implemented in hardware, firmware, or a combination thereof. When implemented in software, the functions above may be stored in a computer readable medium or transmitted as one or more instructions or codes on the computer readable medium. A computer readable media includes a computer storage medium and a communication medium, with the communication medium including any medium that facilitates transfer of a computer program from one location to another. A storage medium may be any available media that may be accessed by a computer. This is used as an example but not limited to: the computer readable medium may comprise random access memory (RAM), read-only memory (ROM), electrically erasable programmable read-only memory (EEPROM), compact disc read-only Memory (CD-ROM) or other optical disc storage, magnetic disk storage medium or other magnetic storage device, or any other medium that may be used to carry or store desired program codes in the form of instructions or data structures and may be accessed by a computer. In addition, any connection may suitably become computer readable medium. For example, if the software is transmitted from a website, a server, or other remote sources by using a coaxial cable, an optical fiber and cable, a twisted-pair line, a digital subscriber line (DSL), or wireless technologies, such as infrared, radio and microwave, then the coaxial cable, the optical fiber and cable, the twisted-pair line, the DSL or the wireless technologies, such as infrared, radio and microwave, are included in the photographic fixing of the medium. As used in the present disclosure, a disk and a disc comprise a compact disc (CD), a laser disc, a compact disc, a digital versatile disc (DVD), a floppy disk, and a Blu-ray disc, wherein the disk usually magnetically copies data, whereas the disc optically copies data by means of a laser. A combination of the above should also be included within the protection scope of the computer readable medium.

In summary, the above description merely represents certain preferred embodiments of the technical solution of the present disclosure, and is not intended to limit the protection scope of the present disclosure. Any modification, equivalent replacement, improvement, etc. made within the spirit and principle of the present disclosure shall be included within the protection scope of the present disclosure.

What is claimed is:

1. A physiological parameter signal fusion processing method comprising:

respectively analyzing at least two physiological parameter signals, so as to obtain a feature of each of the at least two physiological parameter signals;

calculating a signal quality index for each of the at least two physiological parameter signals according to the feature of each of the at least two physiological parameter signals;

displaying the signal quality index for each of the at least two physiological parameter signals as a signal index graph, wherein each signal index graph is dynamically filled to reflect the signal quality index; and determining whether the at least two physiological parameter signals are fused with each other, and when the at least two physiological parameter signals are fused, highlighting the signal index graph corresponding to the physiological parameter signal of the at least two physiological parameter signals that has a highest signal quality index, wherein the at least two physiological parameter signals that are fused are different types of physiological parameter signals; when the at least two physiological parameter signals are not fused, directly displaying the signal index graph for each of the at least two physiological parameter signals.

2. The method of claim 1, wherein highlighting comprises:
highlighting, by means of a color, a graphic and/or an identifier, the physiological parameter signal of the at least two physiological parameter signals that has the highest signal quality index.

3. The method of claim 1, further comprising:
performing a homology determination on the at least two physiological parameter signals according to the features of the at least two physiological parameter signals, so as to obtain a homology determination result for the at least two physiological parameter signals, with the homology determination result comprising being homologous and non-homologous.

4. The method of claim 3, further comprising:
if the homology determination result indicates that at least two physiological parameter signals are homologous, displaying an indication that the at least two physiological parameter signals are homologous.

5. The method of claim 1, further comprising:
calculating a parameter for each of the at least two physiological parameter signals according to the feature of each of the at least two physiological parameter signals; and
correcting the parameter for each of the at least two physiological parameter signals based the respective signal quality indexes of the at least two physiological parameter signals, so as to obtain a fusion parameter for each of the at least two physiological parameter signals.

6. The method of claim 1, wherein each signal index graph is a signal bar graph that comprises plurality of parallel bars that are either filled or empty, and the number of filled bars reflects the signal quality index.

7. A physiological parameter signal fusion processing apparatus, wherein the apparatus comprises:
a processor that respectively analyzes at least two physiological parameter signals, so as to obtain a feature of each of the at least two physiological parameter signals, calculates a signal quality index for each of the at least two physiological parameter signals according to the feature of each of the at least two physiological parameter signals, and determine whether the at least two physiological parameter signals are fused with each other; and
a display device that displays the signal quality index for each of the at least two physiological parameter signals as a signal index graph, wherein each signal index graph is dynamically filled to reflect the signal quality index; when the at least two physiological parameter signals are fused, the display device displays by highlighting the signal index graph corresponding to the physiological parameter signal of the at least two physiological parameter signals that has a highest signal quality index, wherein the at least two physiological parameter signals that are fused are different types of physiological parameter signals.

8. The apparatus of claim 7, wherein the processor is further to perform a homology determination on the at least two physiological parameter signals according to the features of the at least two physiological parameter signals, so as to obtain a homology determination result for the at least two physiological parameter signals, with the homology determination result comprising being homologous or non-homologous.

9. The apparatus of claim 7, wherein the display device is to display an indication that the at least two physiological parameter signals are homologous if the homology determination result indicates that the at least two physiological parameter signals are homologous.

10. The apparatus of claim 7, wherein the processor is to calculate a parameter for each of the at least two physiological parameter signals according to the feature of each of the at least two physiological parameter signals and correct the parameter for each of the at least two physiological parameter signals according to the respective signal quality indexes of the at least two physiological parameter signals, so as to obtain a fusion parameter for each of the at least two physiological parameter signals.

11. The apparatus of claim 7, wherein each signal index graph is a signal bar graph that comprises a plurality of parallel bars that are either filled or empty, and the number of filled bars reflects the signal quality index.

* * * * *